United States Patent
Wise et al.

(10) Patent No.: US 8,501,397 B2
(45) Date of Patent: Aug. 6, 2013

(54) ENRICHMENT OF STEM CELLS FROM ADULT TISSUES

(75) Inventors: Gary E. Wise, Conroe, TX (US); Shaomian Yao, Baton Rouge, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 12/842,754

(22) Filed: Jul. 23, 2010

(65) Prior Publication Data

US 2011/0020930 A1 Jan. 27, 2011

Related U.S. Application Data

(60) Provisional application No. 61/228,245, filed on Jul. 24, 2009.

(51) Int. Cl.
*A01N 1/02* (2006.01)
*C12N 15/85* (2006.01)

(52) U.S. Cl.
USPC ............................................. 435/2; 435/325

(58) Field of Classification Search
None
See application file for complete search history.

(56) References Cited

U.S. PATENT DOCUMENTS

2003/0049238 A1* 3/2003 Rader et al. ................. 424/93.21
2010/0291042 A1* 11/2010 Crawford et al. ............ 424/93.7

FOREIGN PATENT DOCUMENTS

WO    WO 0028813    *  5/2000

OTHER PUBLICATIONS

Cipolleschi et al (Blood, 1993. vol. 82, pp. 2031-2037).*
Uchida et al (The Journal of Clinical Investigation, 2001. vol. 108, No. 7, pp. 1071-1077).*
Ma et al (Oncogene, 2008. vol. 27, pp. 1749-1758).*
Wuertz et al (Spine (Phila Pa 1976). Author manuscript, available in PMC Oct. 14, 2008).*
Lennon et al (Journal of Cellular Physiology, 2001. vol. 187, pp. 345-355).*
Zhou et al (Nature Medicine, 2001. vol. 7, pp. 1028-1034).*
Allen et al (Cancer Research, 1999. vol. 59, pp. 4237-4241).*
Norgaard et al (Ann. N. Y. Acad. Sci. 2006, vol. 1067: pp. 443-447).*
Bosshardt, D.D. et al., "Cementogenesis reviewed: a comparison between human premolars and rodent molars," *Anat Rec*, vol. 245, pp. 267-292 (1996).
Cahill, D.R. et al., "Tooth eruption: evidence for the central role of the dental follicle," *J Oral Pathol*, vol. 9, pp. 189-200 (1980).
Diekwisch, T.G.H., "The developmental biology of cementum," *Int J Dev Biol*, vol. 45, pp. 695-706 (2001).
Handa, K. et al., "Cementum matrix formation in vivo by cultured dental follicle cells," *Bone*, vol. 31, pp. 606-611 (2002).
Luan, X. et al., "Dental follicle progenitor cell heterogeneity in the developing mouse periodontium," *Stem Cells Dev*, vol. 15, pp. 595-608 (2006).
Marks, S.C., Jr. et al., Experimental study in the dog of the non-active role of the tooth in the eruptive process. *Arch Oral Biol* 29:311-322 (1984).
Morsczeck, C. et al., "Isolation of precursor cells (PCs) from human dental follicle of wisdom teeth," *Matrix Biol*, vol. 24, pp. 155-165 (2005).
Research Descriptions from the Grant proposal submitted to NIH, and funded in Mar. 2009.
Saito, M. et al al.l, "Immortalization of cementoblast progenitor cells with Bmi-1 and TERT," *J Bone Miner Res*, vol. 20, pp. 50-57 (2005).
Wise, G.E. et al., "Cellular, molecular, and genetic determinants of tooth eruption," *Crit Rev Oral Biol Med*, vol. 13, pp. 323-334 (2002).
Wise, G.E. et al., "Regional differences of expression of bone morphogenetic protein-2 and RANKL in the rat dental follicle," *Eur J Oral Sci*, vol. 114, pp. 512-516 (2006).
Wise, G.E. et al., "CSF-1 regulation of osteoclastogenesis for tooth eruption," *J Dent Res*, vol. 84, pp. 837-841 (2005).
Yao, S. et al., "Differentiation of Stem Cells in the Dental Follicle," Journal of Dental Research, vol. 87, No. 8, pp. 767-771 (2008).
Yao, S., "Isolation and Differentiation of Dental Follicle Stem Cells," a powerpoint presentation on Dec. 10, 2009 made internally to Department of Comparative Biomedical Sciences, School of Veterinary Medicine, Louisiana State University.
Zeichner-David, M. et al., "Role of Hertwig's epithelial root sheath cells in tooth root development," *Dev Dyn*, vol. 228, pp. 651-663 (2003).

* cited by examiner

*Primary Examiner* — Celine Qian
(74) *Attorney, Agent, or Firm* — John H. Runnels; Bonnie J. Davis (57) ABSTRACT

Subjecting a heterogeneous cell population (one with both stem cells and non-stem cells) to extreme stress selectively eliminated the non-stem cells and resulted in the enrichment of stem cells in the population. The stress can take many forms, including without limitation, cell toxins, high temperature, high salt, and low oxygen (hypoxic) conditions. The number of stem cells remaining after stress were increased, and showed increased expression of traditional stem cell markers. The stem cells were shown to be capable of proliferation and differentiation into multiple types of cells. This method allows purification of stem cells from adult heterogeneous cell populations on a large scale basis without requirement of expensive equipment, and without requiring the presence of cell surface markers. Stem cells produced by the above method can be used for clinical applications, including tissue engineering.

4 Claims, 7 Drawing Sheets

Fig. 3B  DFSCs

Fig. 3A  DFCs

ENRICHMENT OF STEM CELLS FROM ADULT TISSUES

The benefit of the 24 Jul. 2009 filing date of U.S. provisional patent application 61/228,245 is claimed under 35 U.S.C. §119(e).

This invention was made with government support under grant number R01 DE008911, awarded by the National Institutes of Health. The government has certain rights in this invention.

This invention pertains to methods and kits to enrich the number of adult stem cells in a heterogeneous cell population and to isolate adult stem cells by subjecting the heterogeneous cell population to one or more extreme stresses, such as high temperature, high osmotic fluids, and known cell toxins.

Stem Cells. Use of stem cells to regenerate or repair damaged or defective tissues is a promising strategy to cure many human diseases and disorders. Stem cells can be classified into embryonic stem cells, cord-blood-derived embryonic like stem cells and adult stem cells based on their sources. Embryonic stem cells are from early embryos and are pluripotent. Adult stem cells are undifferentiated cells found throughout the body. Current culture techniques suggest that adult stem cells are multipotent; i.e., they can only differentiate to limited cell types under current techniques although some adult stem cells have shown plasticity (see review by Raff 2003). A major advantage of using adult stem cells is that the patient's own cells could be isolated, expanded and induced to differentiate or regenerate for that same patient. In turn, the cells derived or tissue regenerated from the stem cells would not be rejected by the patient's immune system upon transplantation.

One major challenge to overcome in the application of adult stem cell therapy is to be able to identify, isolate and purify the adult stem cells and then proliferate sufficient quantities of the stem cells. Purification of stem cells can be very difficult because of their rarity. For example, in primary isolated dental pulp cells, 0.2%-0.7% cells are colony-forming cells, which are putative stem cells (Gronthos et al., 2000). Therefore, for application of stem cell technology it is necessary to develop efficient and reliable techniques that can isolate primary stem cells from adult tissues. Because adult stem cells may only divide limited times in vitro; e.g; 80% of stem cells from human dental pulp could not proliferate over 20 population doublings (Gronthos et al., 2002), starting with a pure population of such cells is necessary for obtaining an adequate number for subsequent differentiation and tissue engineering.

Stem cells were originally thought to be present only in organs that have high cell turnover rates such as blood, skin, gut, and testis, but it is likely that most, if not all, adult organs contain stem cells. In that vein, stem cells have been identified or isolated from various dental tissues including dental pulp (DPSCs), periodontal ligament and dental follicle (Gronthos et al., 2000; Seo et al., 2004; Morsczeck et al., 2005; Iohara et al., 2006; Jo et al., 2007). When cultured tooth bud cells from 4 day postnatal rats were implanted onto scaffolds, tooth tissues were generated (Duailibi et al., 2004). Dental pulp appears to contain subpopulations of stem cells because single cell colonies derived from pulp cells show diversity in cell surface markers (Gronthos et al., 2000). DPSCs have capabilities to form odontoblast-like and osteoblast-like cells (Braut et al., 2003; Mina and Braut 2004). Thus, stem cells exists in dental tissues with the possibility of using them in stem cell therapy and tissue engineering of dental tissues in vivo (review by Shi et al., 2005).

The dental follicle (DF), a loose connective tissue sac that surrounds the unerupted tooth, plays different roles in the life of a tooth. Its presence is required for eruption (Cahill and Marks, 1980; Marks and Cahill, 1984) whereby it appears to regulate the osteoclastogenesis and osteogenesis needed for eruption (e.g., see review by Wise and King, 2008; Wise et al., 2005; Wise and Yao, 2006). As the tooth pierces the gingiva, the DF differentiates into the periodontal ligament (PDL) to anchor the tooth in its socket to the surrounding alveolar bone. In addition to this differentiation of the DF to form the fibroblasts of the PDL, some DF cells are thought to differentiate into the cementoblasts of the tooth, as well as perhaps some of the osteoblasts of the alveolar bone (e.g., see review by Bosshardt and Schroeder, 1996). Although some studies suggest that some of the cementoblasts may arise from Hertwig's epithelial root sheath, as well as from the DF (Zeichner-David et al., 2003), other studies indicate that all of the cementoblasts arise from the DF (Diekwisch, 2001).

Stem cells appear to be present in the DF of human wisdom teeth (Morsczeck et al., 2005) and in the mouse DF (Luan et al., 2006). Three DF cell lines were cloned, one of which likely was the fibroblastic DF cells that form the PDL, another that remained undifferentiated, and a third that exhibited mineralization behavior as seen by von Kossa staining. Injection of bovine dental follicle cells into immunodeficient mice results in the formation of cementum, as detected by an anti-cementum attachment protein (Handa et al., 2002). More recently, a cementoblast progenitor cell line from bovine DF cells has been isolated and immortalized (Saito et al., 2005).

According to the International Society for Stem Cell Research, dental pulp stem cells (DPSCs) are believed to be "younger" than other adult stem cells, which means that they can be maintained in culture for a longer period of time, and they can differentiate into a variety of cell types such as neuronal and adipose tissue (Gronthos et al., 2002; review by Liu 2006). DPSCs presented more striking odontogenic capability than bone marrow stromal stem cells (Yu et al., 2007). Another advantage is that the dental pulp is an accessible tissue source in deciduous teeth shed by children. Stem cells have also been isolated from human exfoliated deciduous teeth, i.e., SHED (Miura et al., 2004), and these stem cells were able to repair calvarial defects (Seo et al., 2007). The dental pulp can be collected at that time and patient-specific stem cells can be purified from the pulp, expanded and stored for future uses for the given individual. In addition, the pulp can also be obtained from extracted teeth.

Isolation of Stem Cells. Isolation of stem cells from dental tissues has often relied on their adherent and colony-forming properties on a culture surface. For example, such colony-forming method has been used to isolate pulp stem cells from human third molars (Gronthos et al., 2000), and from human exfoliated deciduous teeth (Miura et al., 2004). Such isolation techniques are labor-intensive, time-consuming and skill-demanding because the cloning rings have to be placed over the colonies one by one under a microscope. In addition, the colony formation requires 2 weeks incubation time (Gronthos et al., 2000; review by Liu et al., 2006). In addition, the isolation did not yield a uniform stem cell population; i.e., colonies derived from heterogeneous dental pulp cells show diversity in cell surface markers (Gronthos et al., 2000).

To select a pure population of dental pulp stem cells, immunomagnetic bead sorting has been employed. Briefly, the technique involved binding of an antibody of a stem cell marker to the potential stem cells, then binding of IgG-conjugated magnetic beads to the primary antibody, followed by collecting of the bead-positive cells (review by Liu et al., 2006). For application of the technique, stem cell specific surface markers must exist. If no unique stem cell-specific surface marker is present, selection must be repeated with multiple markers, which greatly increases the cost while reducing the efficacy of the method.

Other techniques used to purify stem cells may be based on cell size (Hung et al., 2002); adherent properties to tissue culture surface (review by Owen & Friedenstein 1988; Caplan 1991; Kuznetsov et al., 1997; Pittenger et al., 1999); or marker dependent sorting such as fluorescence-activated cell sorting (FACS). Since both stem cells and non-stem cells vary in sizes and adherent ability, isolation of stem cells based on size and adherent properties are not specific enough to obtain a pure population of stem cells (Vacanti et al., 2001; Young et al., 2004; Leong et al., 2004). For example, adherent single cell derived colonies of progenitors isolated from bone marrow display a wide variation in cell morphology and growth potential (review by Bianco and Robey 2000). In marker dependent sorting, the problem often encountered is the lack of specific and easily detectable markers. Furthermore, reliable FACS sometimes requires large-frame ion lasers. For example, for sorting of side population stem cells, an expensive UV laser is required. In addition, the high fluid pressure during sorting might damage the biological activity of the sensitive cells, as discussed by Gangopadhyay et al., (2004). Thus, development of a simple, inexpensive and precise technique of isolating a pure population of stem cells is needed.

In an injury or diseased tissue, the existing stem cells can act as a repairing mechanism. Stem cells possess some unique properties. For example, ABC transporters are one of the largest and most ancient protein pumps responsible for the efflux of many molecules such as the DNA binding dyes, rhodamine and Hoechst from cells (Goodell et al., 1996; Wolf et al., 1993; Zhou et al., 2001). Effluxes of those dyes prevent or reduce the toxicity of the given chemical to the cells. Members of the ABC transporter super-family, BCRP1 and MDR1 (P-glycoprotein), have been identified as stem cell markers because a significantly higher level of these proteins are sited on the membrane of stem cells. Studies also indicate that stem cells produce high levels of aldehyde dehydrogenases (ALDHs) to detoxify aldehydes (Cai et al., 2004; Storms et al., 1999).

Substrates of BCRP and ALDHs have been used to develop flow cytometry based methods to isolate stem cells from various tissues. When Hoechst 33342 is added to a heterogeneous population of cells, cells with a higher level of BCRP, such as stem cells, will efflux more molecules of the dye, and thus result in a dull staining of their nuclei (Goodell et al., 1996). Such cells can be sorted out as a population, termed "side population," by flow cytometry. Side population cells have been isolated from multiple tissues including hematopoietic compartments (Goodell et al., 1997; Uchida et al., 2001), skeletal muscle (Gussoni et al., 1999; Jackson et al., 1999), brain (Hulspas et al., 2000) and dental pulp (Iohara et al., 2006). Additionally, embryonic stem cells also show side population phenotype (Zhou et al., 2001), indicating they are also equipped with a high level of BCRP pumps. Side population cells have been proved to be highly enriched for stem cells or primitive stem cells (Lin and Goodell 2006; Wolf et al., 1993; Leemhuis et al., 1996; Redvers 2006, Parmar et al., 2003).

Similarly, stem cells have been identified based on the ability to efflux other fluorescence dyes that are substrates, such as rhodamine-123, of ABC transporters (Orlic et al., 1993). However, as stated earlier, isolation of side population cells requires expensive flow cytometry with a special UV. Another limitation is that only the substrates that have distinct fluorescence emission can be used. Substrates that are highly efficient for the enzymes, and thus of low toxicity to the stem cells, can not be used if they are non-fluorescent. This limitation also applies to other types of substrates, such as the substrates of ALDHs. Some of the known substrates of ABC transporters are listed in Table 1 (review by Doyle and Ross 2003).

TABLE 1

Some substrates or drugs of ABC transporters

| | | | | |
|---|---|---|---|---|
| Mitoxantrone | Idarubicinol | topoisomerase I | Pheophorbide a | Protoporphyrin |
| Topotecan | Flavopiridol | Zidovudine | Daunorubicin | Prazocin |
| Irinotecan, SN-38 | CIIO33 | lamivudine | Epirubicin | Indolocarbazole |
| 9-Aminocamptothecin | BBR3390 | Rhodamine 123 | Hoechst 33342 | Prazocin- |
| Doxorubicin (DOX) | Methotrexate | Lysotracker | | |

ALDHs are a group of intracellular enzymes that catalyze oxidation reactions to convert cytotoxic aldehyde to non-toxic or low-toxic carboxylic acid, thus resulting in cellular detoxification. ALDHs play an important role in the metabolism of ethanol, vitamin A, and cyclophosphamide. Recent advances in ALDHs research suggested that stem cells share the common characteristic of having a high level of ALDHs (Cai et al., 2004; Storms et al., 1999). For example, hematopoietic progenitors, hematopoietic stem cells (HSC) and intestinal crypt stem cells display high levels of cytosolic ALDHs. Accordingly, those cells are relatively resistant to cyclophosphamide (Kastan et al., 1990; Russo et al., 1989). This high ALDHs activity also appears to relate to the colony-forming ability of stem cells over time (Lioznov et al., 2005).

ALDHs were thought to be telltale markers that distinguish stem cells from other non-stem cells. The fluorescent substrates of the enzymes, such as AldeFluor, have been used in flow cytometry-based isolation to purify stem cells from multiple tissues, including neural stem cells from brain (Corti et al., 2006) and hematopoietic stem cells from cord blood (Hess et al., 2005). ALDHs have a broad substrate list including acetaldehyde and many biogenic amines.

Humans and other mammals maintain a constant body temperature at 37° C. in most tissues and organs. Alteration of body temperature, especially fever, is a frequently occurring symptom in many medical conditions. Fever may have evolved as a host defense mechanism through millions of years of evolution (review by Schaffner 2006; Soszynski 2003). Elevated body temperature creates a hostile environment for some pathogens (Fischler and Reinhart, 1997). However, elevated temperature changes the micro-environment in the cytoplasm, and affects many biochemical processes. In extreme circumstances, it can impair cell functions and cause cell death (Harris, 1967). Some cells produce heat shock proteins to prevent cellular damage by heat stress (Li et al., 1992). A heat shock protein, HSP105, has been shown to protect cancer cells from apoptosis induced by heat shock (Hosaka et al., 2006). Evidence suggests that cancer cells are derived from the transformation or mutation of normal stem cells (review by Reya et al., 2001).

Another stress of cells often encountered is hypoxia in which severe and prolonged hypoxia can result in cell injury and death (Lennon et al., 2001). A study of cell survival in hypoxic conditions reported that BCRP−/− (lack of functional BCRP) progenitor cells are more susceptible to hypoxic conditions than are their counterpart wild type BCRP+/+ cells (Krishnamurthy et al., 2004). The protective effect of BCRP is the result of its specifically binding to heme to prevent porphyrins accumulation. Such accumulation is detrimental to cells under hypoxic conditions. Additionally, hypoxia enhances BCRP expression to fortify such effect. When isolated mesenchymal stem cells were subjected in hypoxic conditions (5% O2), they proliferated more rapidly and formed more colonies than they did in normal (20% O2) conditions (Lennon et al., 2001).

We have discovered that subjecting a heterogeneous cell population (one with both stem cells and non-stem cells) to extreme stress selectively eliminates the non-stem cells and thus results in the enrichment of stem cells in the population. The stress can take many forms, including without limitation, cell toxins, high temperature, high salt, and low oxygen (hypoxic) conditions. We have shown that a greater percentage of the cells remaining after stress are stem cells based on traditional stem cell markers. We have also shown that these cells are capable of proliferation and differentiation into multiple types of cells. This method allows purification of stem cells from adult heterogeneous cell populations on a large scale basis without requirement of expensive equipment, and without requiring the presence of cell surface markers. Stem cells produced by the above method can be used for clinical applications, including tissue engineering.

We have identified stem cells in the dental follicles (DF) of the rat first mandibular molar by Hoechst staining, alkaline phosphatase staining, and expression of side population stem cell markers. These cells were shown to be able to differentiate into osteoblasts, adipocytes and neurons. Treating the DF cell population with doxorubicin (DOX) followed by incubation in an adipogenesis medium indicated that stem cells were isolated and differentiated into adipocytes. We have shown that doxyrubicin (DOX) is effective in enriching the percent stem cells in a cell population, and believe that other cell toxins will also work, for example, mitoxantrone (MXR) and acetaldehyde (ACH). We believe that any substrate for the ATP-binding cassette transporters ABCB1 (also known as P-glycoprotein (P-gp) and multi-drug resistance protein (MDR1)) and ABCG2 (also known as breast cancer resistance protein (BCRP1) or aldehyde dehydrogenase will work to select the stem cells. Some of these substances are listed in Table 1.

We have also shown that exposure to stresses of heat, salt and low oxygen will also selectively kill the non-stem cells. We have shown that exposure of an adult heterogeneous cell population (dental follicle cells) to heat at about 44° C., high salt at about 619 to about 623 mmol/kg osmolality, and low oxygen (levels below 21%) resulted in a higher percentage of stem cells surviving the exposure than the non-stem cells.

Without wishing to be bound by this theory, we believe that the above enrichment of stem cells upon exposure to cell toxins or high stresses is due to the self-protective mechanisms that stem cells which enable them to exist under conditions that normal cells cannot. The number of stem cells in a heterogeneous population can be enriched by taking advantage of these self-protective mechanisms and subjecting the heterogeneous population to one or more stress conditions and eliminating the non-stem cells in the population.

The current protocols for purification of stem cells from dental tissues are labor intensive, somewhat vague and often expensive. In contrast, we have developed safe, simple and efficient techniques to purify stem cells from dental tissues. We believe that one function of stem cells in adult tissues is to serve as repair and regeneration systems to replace damaged or defective tissues and organs. To fulfill the repair task, stem cells must first survive the original condition causing the damage. Thus we believe that stem cells possess specific or extra defense protection mechanisms such as anti-stress or anti-drug mechanisms that allow them to survive various stresses.

We have treated dental follicle cells with different cell stresses (e.g., cell toxins, heat or osmotic or oxygen stress), and found that the surviving cells had a higher potential for differentiation into specific tissues, for example, adipocytes and bone cells. We have shown that certain conditions selectively kill non-stem cells and thus increase the stem cell percentage in a heterogeneous cell population. This method of increasing the percent stem cells in a cell population can thus be used to purify stem cells from heterogeneous cell populations. To successfully purify stem cells from a heterogeneous population using this method, the stem cells must have unique features that allow them to be distinguished from the non-stem cells. In this regard, without wishing to be bound by this theory, we believe that the stem cells from dental follicle or pulp are equipped with unique anti-stress (including anti-drug) mechanisms that help them to survive encountered stresses. One or more of the following mechanisms would result in favoring stem cell survival from a stress over non-stem cells survival: (1) the mechanism is stem cell specific; (2) the anti-stress mechanism is more active in stem cells than in other cells, e.g., stem cells express significantly higher levels of detoxification enzymes; (3) only stem cells are able to activate or acquire mechanisms to respond to stress; (4) stem cells can boost/fortify their anti-stress mechanism(s) to a higher level than do non-stem cells to respond to given stresses; and (5) the anti-stress mechanisms of stem cells are longer-lasting than those of non-stem cells.

Stem cells have been shown to be equipped with a high level of certain ABC transporters and ALDHs to detoxify the defined substrate chemicals. We have determined the dosage and duration of doxorubicin (DOX), a substrate of BCRP1 and MDR1 (both members of ABC transporters), needed to kill the non-stem cells in the cultured dental follicle and dental pulp cells. We also believe that Mitoxantrone (MXT), another substrate of ABC transporters, could be used to increase the percentage of stem cells. Other substrates of ABC transporters as listed in Table 1 are known and should work in this method. Similar experiments were conducted with a substrate of ALDHs, 4-hydroxyperoxycyclopho-sphamide (4-HC), and again the stem cells were increased in the population. Another substrate of ALDHs that should work in increasing the stem cell percentage is acetaldehyde (ACH). After a given treatment of drug or substrate, the cell survival rates were assessed, and the surviving cells were subjected to proliferation and differentiation analyses. In all tests, the surviving stem cells were able to proliferate and differentiate.

Alteration of body temperature and shortage of oxygen supply (hypoxia) are frequent medical conditions in humans and other mammals. Severe thermal and/or hypoxic stresses can result in cell or tissue damage or death. We also have shown that some dental follicle and pulp cells can survive thermal or hypoxic stresses, and that the surviving cells have stem cell properties of proliferation and differentiation. In addition, using RT-PCR technology, we have shown that the surviving cells from heat stress have increased gene expression of stem cell markers over the expression in control cells not exposed to heat stress. Using PCR arrays, we will compare the expression of the markers between (1) the original cell population and its derivative putative stem cell populations (i.e., sub-populations) obtained by different optimized protocols; (2) the stem cell sub-population to each other (e.g., are the stem cells derived from BCRP substrate treatment similar to those derived from hypoxia?). We will combine the gene expression data with proliferation and differentiation data to conduct correlation analysis using Statistical Analysis Software (SAS). This will characterize the sub-populations surviving from different stresses on a molecular basis, and ultimately will help select the stem cells best suited for tissue engineering.

EXAMPLE 1

Stem Cell Enrichment from Dental Follicle of a Rat

Establishment of cell cultures from rat dental follicle: Dental follicles (DF) were surgically removed from the first mandibular molars of Sprague Dawley rat pups at days 5-7 postnatally, and the isolated DF cells then suspended in MEM medium containing 10% newborn calf serum (NCS), 1 mM sodium pyruvate and antibiotics as previously described (Wise et al., 1992). Next, 5 ml of the cell suspension was transferred into a T-25 cell culture flask and incubated overnight to allow the cells to adhere. The non-adherent cells then were removed by aspiration and the remaining adherent cells were either grown as previously described by Wise et al., (1992), which are referred to as "DF cells" or "DFCs" or grown in a stem cell growth medium consisting of α-MEM and 20% heat-inactivated fetal bovine serum (FBS), a culture medium that encourages the growth of dental follicle stem cells referred to as "DF stem cells" or "DFSCs." The resulting population of culturing in the α-MEM plus 20% FBS is a heterogeneous cell population containing both dental follicle cells and dental follicle stem cells (DFSCs), but is referred to as "DFSCs". For either culture, upon confluency, the cells were trypsinized and passaged into new flasks until the desired passages were obtained.

Expression of ABC transport genes: Total RNA was extracted from the DFCs of the postnatal rat first mandibular molars (day 1 to day 11) and from the DFSCs of passage 3 with a TRI REAGENT protocol (Molecular Research Center, Cincinnati, Ohio). The RNA samples were digested with DNase I to remove any possible DNA. RNA concentration was measured by optical density at 260 nm and 280 nm with the OD260/OD280 ratio greater than 1.9.

Figure 1A:
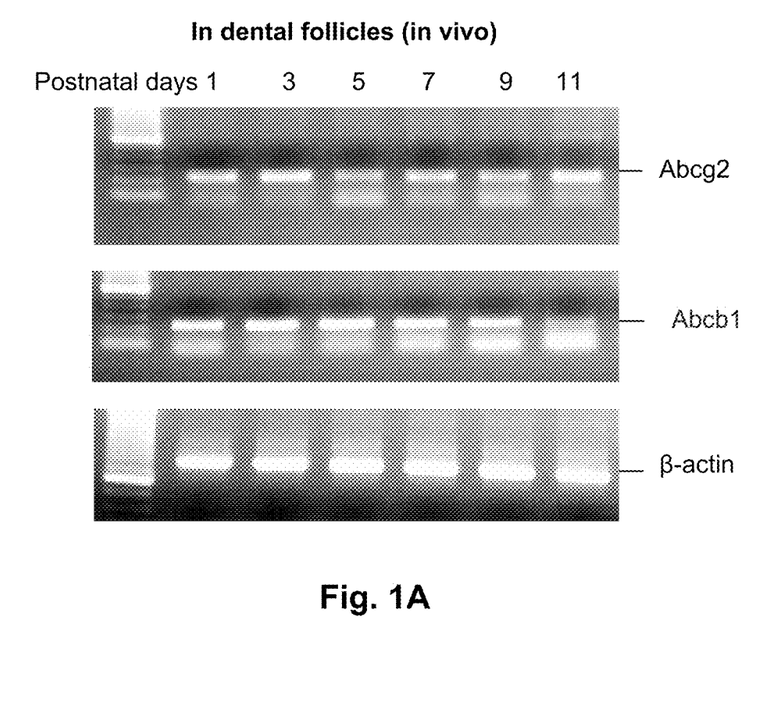
FIG. 1A illustrates the results of RT-PCR showing the expression of some ABC transporters (BCRP ("Abcg2") and MDR1 ("Abcb1")) in vivo in dental follicle cells from rats of various ages.
Figure 1B:
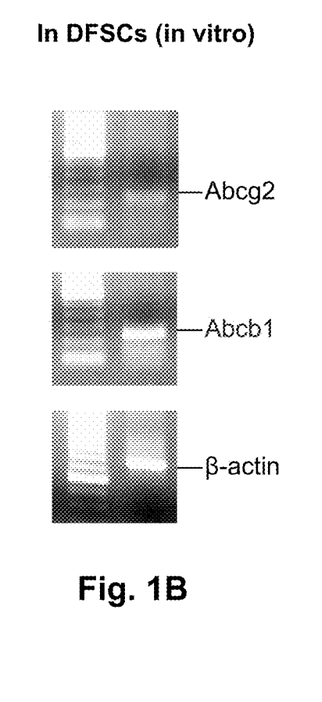
FIG. 1B illustrates the results of RT-PCR showing the expression of some ABC transporters (BCRP ("Abcg2") and MDR1 ("Abcb1")) in vitro in cultured dental follicle stem cells (DFSCs).

Gene expression of side population stem cell markers, Breast Cancer Resistant Protein (BCRP; noted as "Abcg2" on FIG. 1) and Multidrug Resistant Protein 1 (MDR1, noted as "Abcb1" on FIG. 1), were determined by conventional RT-PCR. For this, the RNA was reverse-transcribed into cDNA with reverse transcriptase (Invitrogen, Carlsbad, Calif.). The PCR was conducted by mixing cDNA with gene specific primers, dNTP, PCR buffer and Taq DNA polymerase followed by running 30 thermal cycles at denaturing 94° C. 45 sec, annealing 58° C. 1 min and extension 72° C. 1 min. PCR was also conducted in parallel to amplify the β-actin gene that served as the control. The primer sequences for BCRP (Abcg2) were as follows: 5'AGTCCGGAAAACAGCT-GAGA3' (forward; SEQ ID NO.1), 5'CCCATCACAACGT-CATCTTG 3' (reverse; SEQ ID NO.2). The primer sequences for MDRI (Abcb1) were as follows: 5'GGA ACT CTC GCT GCT ATC ATC CAC GGA AC 3' (forward; SEQ ID NO.3), 5'ACC TGG ATG TAG GCA ACG ATG AGC ACA CC3' (reverse; SEQ ID NO:4). PCR products were electrophoresed in a 1% agarose gel and visualized under UV light.

Cell growth and Differentiation Experiments: To characterize the cell growth in culture, DFCs and DFSCs at passage 3 and passage 9 were seeded in 3 cm diameter tissue culture Petri dishes and cultured with appropriate media (i.e., DF cells in MEM+10% NCS+sodium pyruvate; DF stem cells in α-MEM+20% FBS). To monitor for stem cells, cultures of either DF cells or DF stem cells were fixed in neutral-buffered formalin after culturing for 1, 3, 5, 7, 9, 11, 13 and 15 days, and then stained for alkaline phosphtase (ALP) activity by incubating in ALP substrate solution containing 0.01% Naphthol AS-Mx phosphate for 15 min at room temperature. To determine if the cells could differentially pump out Hoechst, the substrate of BCRP, Hoechst 33342 was added into the culture medium at a final concentration of 0.2 μg/ml and then examined under a inverted fluorescence microscope for blue nuclear staining after 20 min of incubation. Unless otherwise noted, the commercial source for the chemicals is Sigma-Aldrich (St. Louis, Mo.).

To determine the differentiation capabilities of the putative stem cells, DFSCs were subjected to various differentiation procedures. For osteogenesis, cells were cultured for 2 weeks in medium consisting of DMEM-LG, 10% FBS, 50 µg/ml ascorbate-2 phosphate, $10^{-8}$ M dexamethasone, and 10 mM β-glycerophosphate for 3 weeks as previously described, followed by von Kossa and Alizarin Red staining to assess for mineral deposition (as described in Hung et al., 2002). For adipogenesis, DFSCs were cultured for 2 weeks in medium consisting of DMEM-LG, 10% FBS (Invitrogen Corporation, Carlsbad, Calif., USA), 50 µg/ml ascorbate-2 phosphate (Sigma-Aldrich), $10^{-7}$ M dexamethasone, and 50 µg/ml indomethacin, with a medium change every 3 days (Hung et al., 2002). The cells then were stained with Oil red 0 to evaluate adipogenesis.

To induce neurogenesis, DFSCs were initially treated in a transition medium consisting of DMEM-LG with 10% FBS and 10 ng/ml basic fibroblast growth factor for 24 hours. Next, the cells were incubated in the neuronal induction medium consisting of DMEM-LG, 2% DMSO, 200 µM butylated hydroxyanisole, 25 mM KCL, 2 mM valporic acid, 10 µM forskolin, 1 µM hydroxycortisone, 5 µg/mL insulin, and 2 mM L-glutamine. After 24 hours of incubation, the cells were fixed and immunostained for neurofilament-200. Briefly, cells were fixed in cold methanol for 5 min, and incubated with anti-neurofilament-200 (Chemicon, Temecula, Calif.) overnight at 4° C. Immunostaining controls were incubated with rabbit IgG instead of primary antibody. Next, they were incubated with secondary antibody labeled with horseradish peroxidase followed by 3 washes with PBS. The horseradish peroxidase was detected by incubation with 3,3'-diaminobenzidine (DAB) substrate.

When the DFCs were grown in a stem cell growth medium, clusters of cells were formed after two weeks that were not seen when the cells were grown in normal MEM medium. In turn, these clusters stained for alkaline phosphatase (ALP) which, among other things, is a marker for stem cells when it is expressed on the cell membrane. No ALP staining was seen in DF cells grown in normal MEM medium. (Data not shown)

Growing the DF cells in stem cell medium to make the heterogeneous DFSC cell population, and then staining with Hoechst 33342 to detect side population stem cells showed that some 2-4% of the cells weakly fluoresced. This indicates these cells are likely stem cells because stem cells efflux the dye out with BCRP, an ABC membrane transporter. To confirm that the BCRP gene was expressed by the cells, conventional RT-PCR was conducted both in vivo on cells directly taken from the dental follicle and in vitro on the denticle follicle stem cells (DFSCs). The DFs at days 1-11 were examined and all expressed BCRP and MDR1, as did the DFSCs in culture. The results are shown in FIG. 1. Both BCRP and MDR1 expresssion was detected in the DFs of the rat first mandibular molar at postnatal days 1, 2, 5, 7, 9 and 11 in vivo.

Figure 3A:
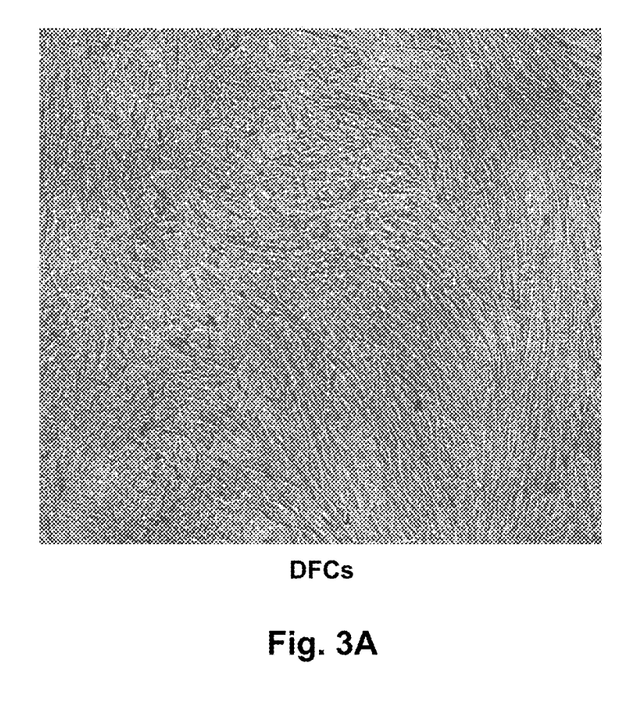
FIG. 3A depicts rat dental follicle cells (DFCs) incubated in a medium to stimulate osteogenesis and then stained with Alizarin red stain for mineralization to indicate any presence of osteogenesis (or bone formation).
Figure 3B:
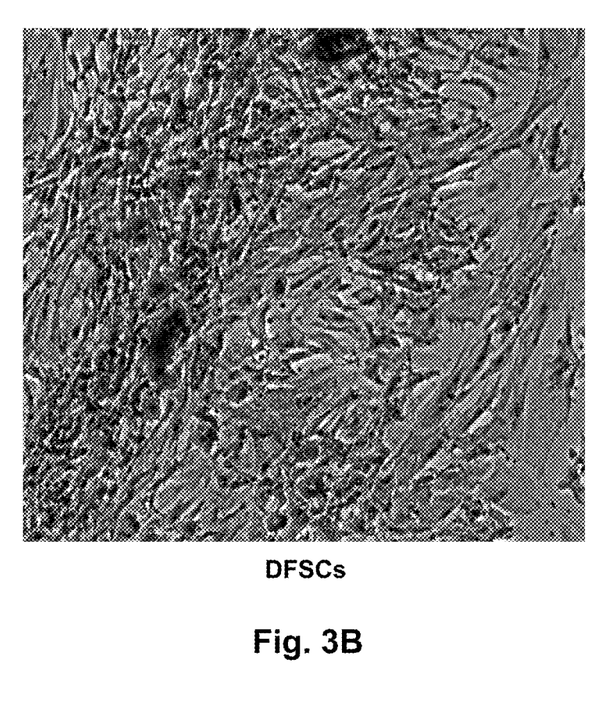
FIG. 3B depicts rat dental follicle stem cells (DFSCs) incubated in a medium to stimulate osteogenesis and then stained with Alizarin red stain for mineralization to indicate any presence of osteogenesis (or bone formation).
Figure 3C:
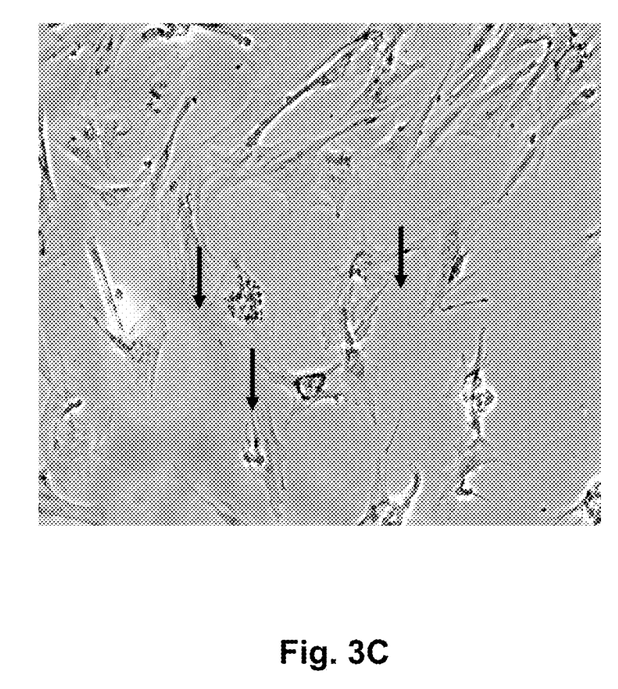
FIG. 3C depicts rat dental follicle stem cells (DFSCs) incubated in a medium to stimulate adipogenesis and then stained with Oil Red O stain to indicate the presence of fat tissues. The arrows indicate the stained adipocytes.
Figure 3D:
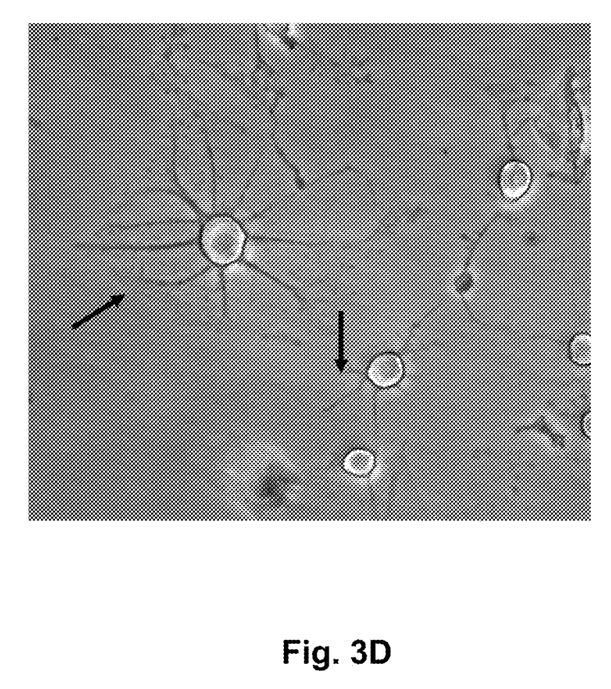
FIG. 3D depicts rat dental follicle stem cells (DFSCs) after incubation in a medium to induce the growth of motor neurons. The arrows indicate the growth of multipolar neurons.

To determine the differentiation capabilities of the putative stem cells, cells grown in the stem cell medium (DFSCs) were placed in different differentiation media. When placed in an osteogenic differentiation medium for 3 weeks, osteoblasts formed and developed mineralization nodules (clusters) as seen by Alizarin red staining and von Kossa staining FIGS. 3A and 3B show the results of staining with Alizarin red stain. No staining was seen in the DFCs even after grown in osteogenesis medium (FIG. 3A) In contrast, DFSCs grown in the osteogenic medium, and then stained, showed the red stain indicating bone deposition or mineralization (FIG. 3B). When cells grown in stem cell medium (DFSCs) were placed in an adipogenic medium for 2 weeks and then stained with Oil Red O, stained adipocytes were observed whereas none were observed in the cells were not placed in the adipogenic medium. (FIG. 3C). Finally, placing DFSCs into a neuronal induction medium for 24 hrs resulted in the development of cells that resembled multipolar neurons. (FIG. 3D) No neurons were seen in the DFSC controls in which the cells were not cultured in the neuronal induction medium. Using a marker for late neuron differentiation, neurofilament protein 200, resulted in immunostaining of the neurons in the induction medium with no immunostaining seen in the controls not placed in the neuron induction medium. Immunostaining controls without primary antibody did not stain. (Data not shown)

EXAMPLE 2

Initial Work with Cell Toxin (DOX) and Thermal Stress

In another experiment to determine to enrich the populations of stem cells, DFSCs were treated with doxorubicin (DOX), a substrate of BCRP, at concentrations of 0.5, 1 or 2 µM for 1, 2, 4 and 6 hrs. The cells were incubated at 37° C. for the designated duration. After the treatment, the cells were collected by centrifugation at 800×g for 5 min, and the cell pellet washed once with growth medium to completely remove the substrate. Then the cells were resuspended in 20 ml of medium and transferred back to the same flask. After 24 hours of incubation, the dead cells were removed by changing the medium, as the viable cells remained attached on the culture surface. The number of viable cells was counted in 5 to 10 randomly selected spots (1 $mm^2$ each) for calculation of the survival rate as the ratio of treatment/control. The surviving cells were placed in an adipogenesis differentiation medium, as previously described.

Figure 2:
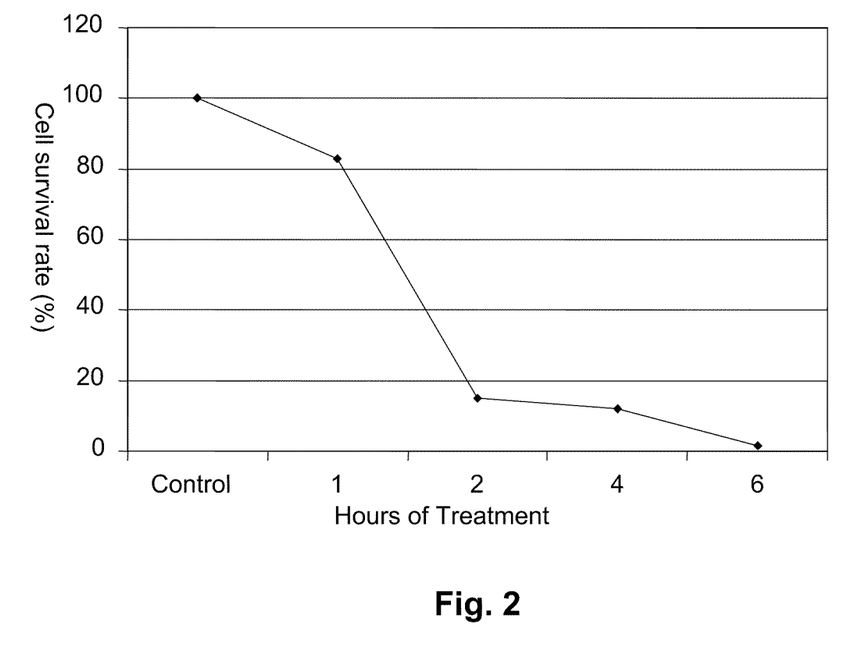
FIG. 2 illustrates the percent cell survival rate in rat dental follicle cells as a function of time exposed to 1 uM doxorubicin (DOX).

Treatment of the DFSCs with doxorubicin (DOX) resulted in the number of surviving cells decreasing as the duration of DOX (1 µM) incubation was increased from 2 hours, to 4 hours and to 6 hours as compared to the control without DOX treatment. The results are shown in FIG. 2. Placing cells that survived treatment with DOX for 4 hours in an adipogenesis induction medium resulted in the majority of the cells forming Oil Red O positive adipocytes. In contrast, in the control DFSCs not treated with DOX, but placed in adipogenesis induction medium, the majority of the cells remained undifferentiated with only a few forming adipocytes, (Data not shown). These results indicate that DOX killed most of the non-stem cells in the DFSC population, and that the surviving stem cells were still capable of differentiation.

EXAMPLE 3

Heat-Shock Enriches Stem Cell Numbers in Dental Follicle Cell Populations

Figure 4:
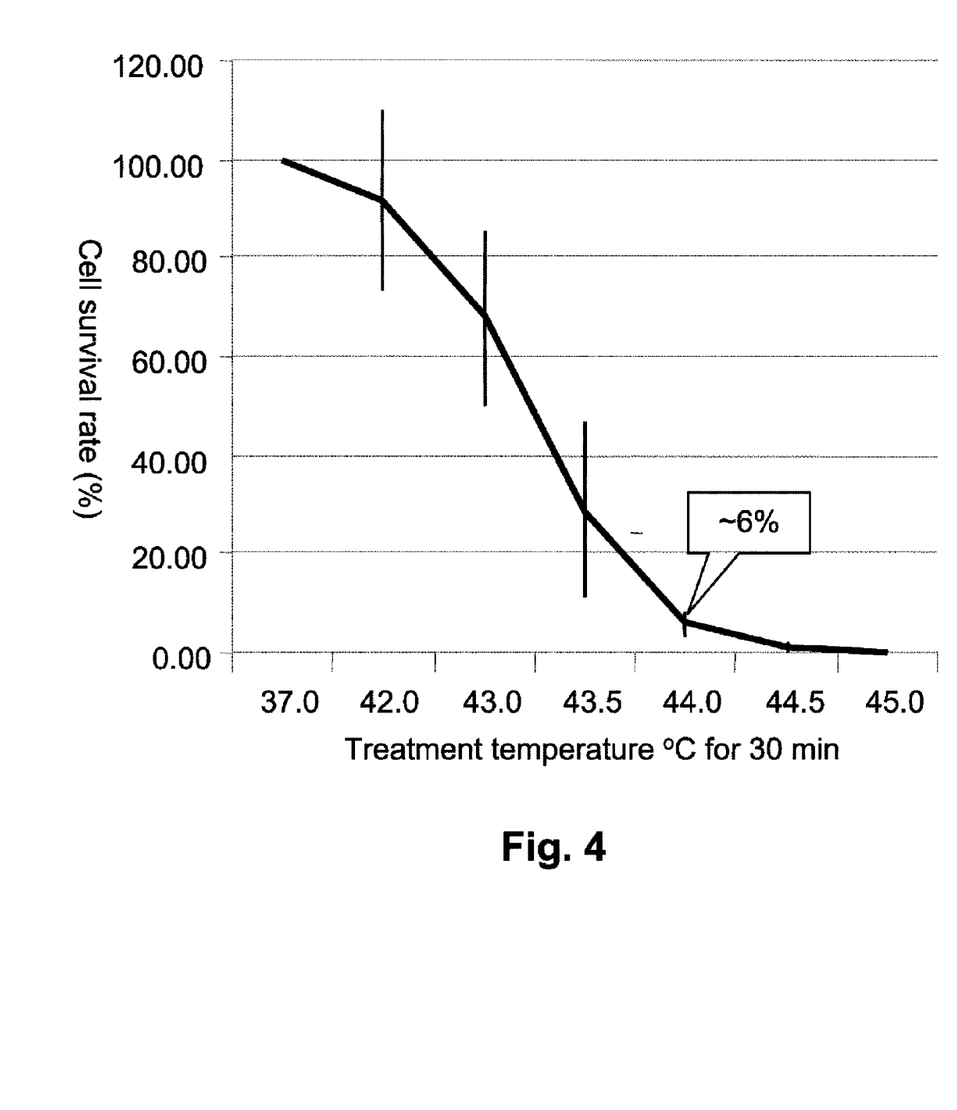
FIG. 4 illustrates the percent cell survival rate in a heterogeneous population of rat dental follicle cells (DFCs) and dental follicle stem cells (DFSCs) as a function of temperature after exposure for 30 minutes.

To determine if heat stress could be a means of enriching a population for stem cells by eliminating non-stem cells from the dental follicle cell (DFC) population, DFCs were obtained from $1^{st}$ mandibular molars of rat pups, as described above. The cells were initially cultured in MEM-α containing 20% FBS to induce the growth of stem cells, and forming a heterogeneous population of non-stem cells and stem cells (DFSCs). To determine the tolerance of this heterogeneous population to heat-shock, DFSCs were suspended in normal culture medium and incubated at temperatures from 37° C. (control) to 46° C. for 30 min. The number of surviving cells was counted as described above. The results are shown in FIG. 4.

Figure 5:
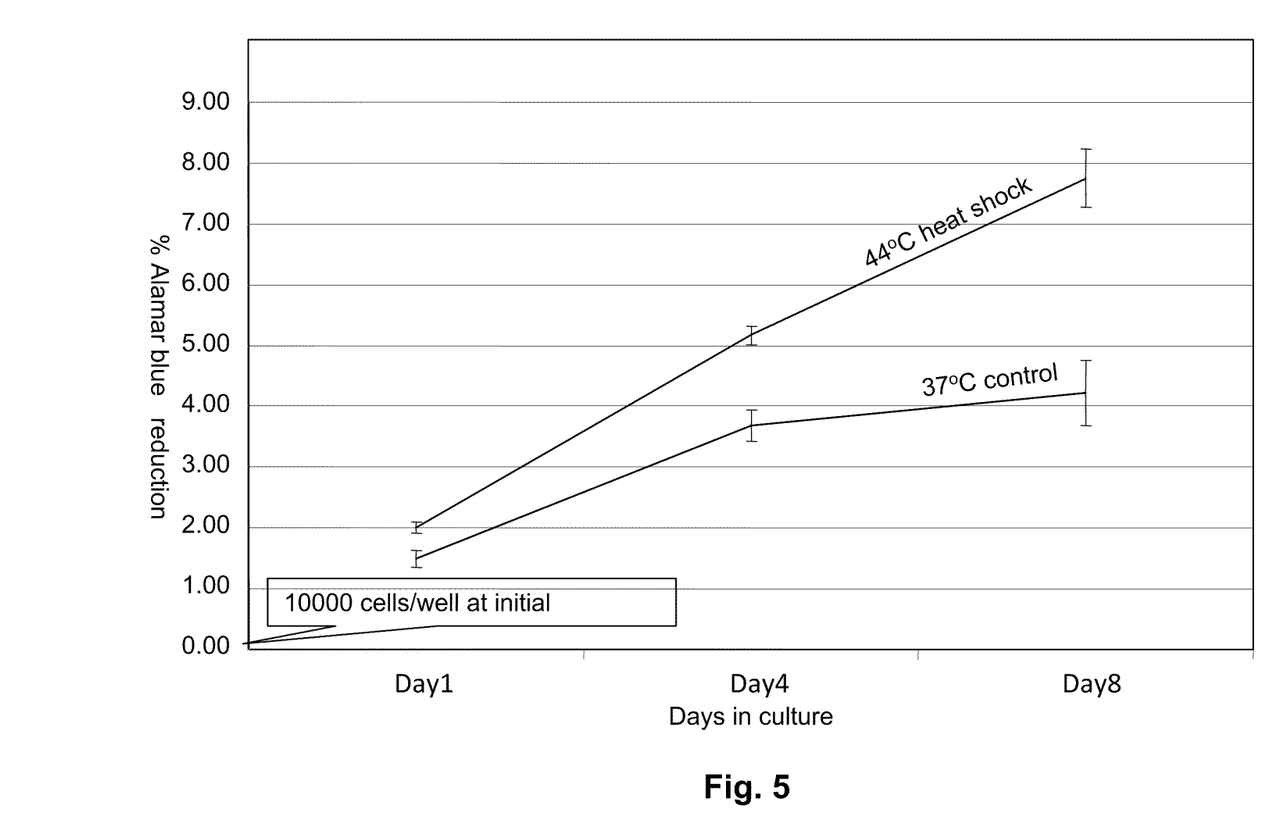
FIG. 5 compares the proliferation rate of two populations of cells cultured under normal conditions as followed using the Alamar blue cell proliferation assay. The control was a heterogeneous populations of cells rat dental follicle cells (DFCs) and dental follicle stem cells (DFSCs) that was only cultured at the normal temperature of 37° C. and never exposed to elevated temperatures. The other population was cells that survived the exposure to 44° C. for 30 minutes (primarily DFSCs).

Proliferation assay: The DFSCs surviving from heat shock at 44° C. heat stress and the DFSCs not subjected to heat stress were each seeded into a 12-well plate at a density of 1000 cells/ml in stem cell growth medium consisting of α-MEM+ 20% FBS. The plates were incubated in normal culture conditions at 37° C. Cell proliferation was monitored with an alamar blue living cell proliferation assay procedures, as previously described (Yao et al., 2006), at days 1, 4, and 8 during incubation. Alamar blue reduction was calculated. The results are shown in FIG. 5, indicating the surviving stem cells were capable of proliferating.

Differentiation assays: To evaluate stem cell properties of heat-tolerant DFSCs, cells surviving from 44° C. were returned to 37° C., and after 3 to 5 days of growth, were induced for osteogenesis or adipogenesis. The surviving cells were tested using 24-well plates with cells seeded as described above in the proliferation assay section. For adipogenesis, cells were placed in an adipocyte induction medium, which consisted of DMEM-LG supplemented with 10% FBS, 50 μg/ml ascorbate-2 phosphate, $10^{-7}$ M dexamethasone, and 50 μg/ml indomethacin, and cultured in a 37° C., 5% CO2 incubator for 2 weeks with a medium change every 3 days. The cells were then stained with Oil Red 0 staining to assess for adipogenesis. For osteogenesis, the induction medium consisted of DMEM-LG, 10% FBS, 50 μg/ml ascorbate-2 phosphate, $10^{-8}$ M dexamethasone, and 10 mM β-glycerophosphate for 2 weeks as previously described, followed by von Kossa and Alizarin Red staining to assess for mineral deposition (as described in Hung et al., 2002).

The threshold temperature for elimination of the majority of the cells was between 44° C. to 44.5° C. (1-6% cells survived; FIG. 4). Cells surviving from 44° C. grew more rapidly upon returning to 37° C. than did the control cells as shown in FIG. 5. When those heat-tolerant cells were placed in a given differentiation medium, both osteogenesis and adipogenesis levels were higher than in the controls not subjected to heat-shock. (Data not shown)

Figure 6:
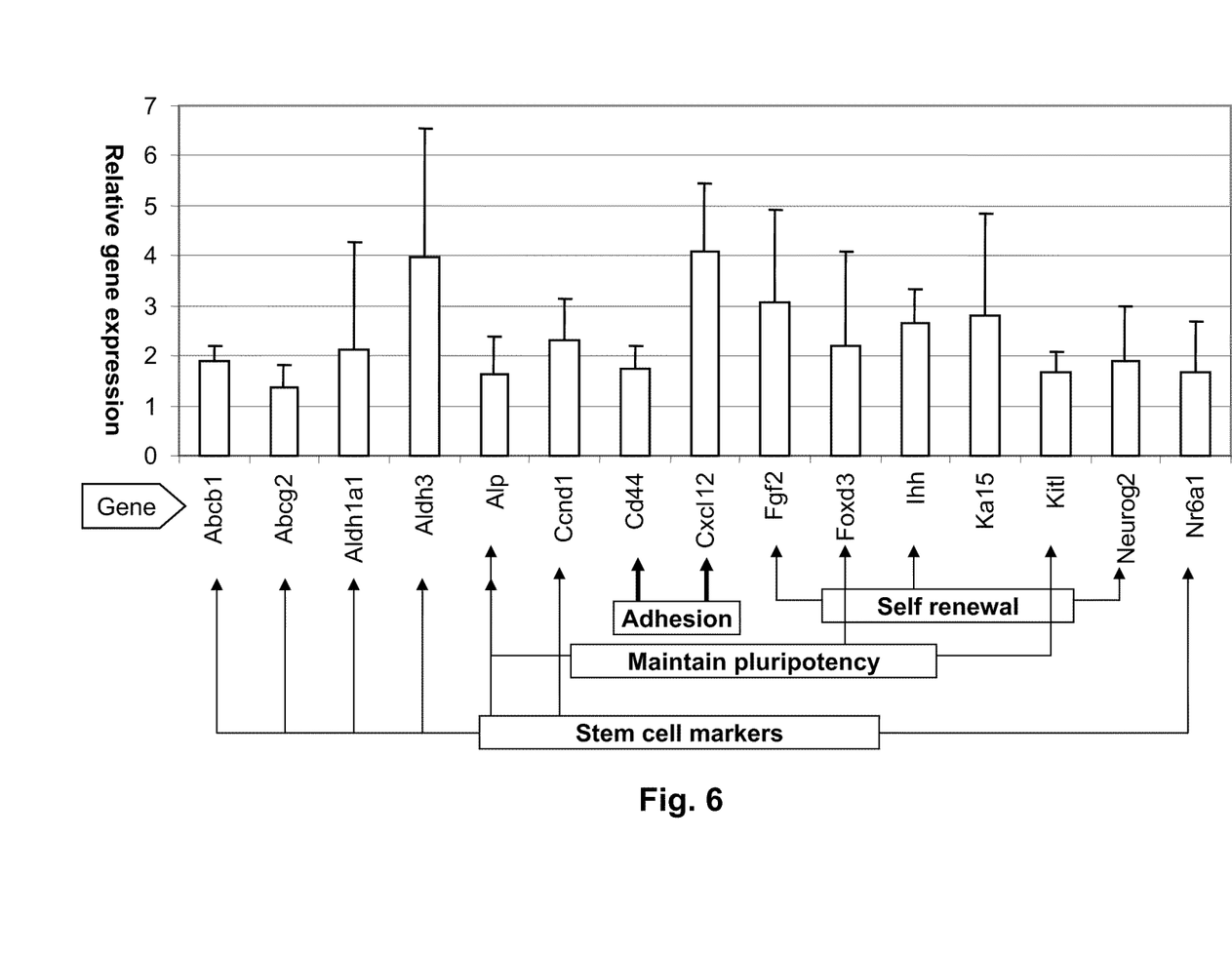
FIG. 6 illustrates the relative increase in expression of selected stem cell-related genes using RT-PCR in putative rat dental follicle stem cells surviving heat shock at 44° C. as compared to the expression of the heterogeneous populations of rat dental follicle cells and rat dental follicle stem cells cultured at 37° C.

In addition, RT-PCR using a stem cell assay from SABiosciences (SuperArrray Bioscience Corporation, Frederick, Md.) was used to assess the relative increase in expression of selected stem cell-related genes in putative rat dental follicle stem cells surviving heat shock at 44° C. over the gene expression of the control rat heterogeneous cell population not exposed to heat shock. The results are shown in FIG. 6.

Stem cell gene expression. For the microarray study, we will use a rat stem cell oligo array (SuperArray Bioscience Corporation, Frederick, Md.) containing 256 genes related to the identification, proliferation and differentiation of various stem cells as previously described (Liu and Wise 2007). The array will be processed according to the manufacturer's protocol. Briefly, RNA will be isolated from the putative stem cells after heat exposure and from their counterpart unselected cells. RNA will then be labeled with biotin-16-dUTP for hybridization with the array. Followed by washes to remove unbound cRNA, the cRNA bound to the matching gene specific oligos printed on the membrane will remain. Finally, the bound cRNA on array will be detected using chemiluminescence, and an image captured with an imaging system. The image will be loaded into the GEArray Expression Analysis Suite program (SuperArray Bioscience Corporation) to acquire the intensity of each gene and then normalized to one of the house-keeping genes (control). The changes in expression of the markers in a given putative stem cell population will be calculated by comparing the given population to its counterpart unselected population.

Heat-shock was shown to kill mostly non-stem cells, such that the remaining population consisted primarily of stem cells, cells shown to have increased gene expression for typical stem cell genes. The remaining stem cells were shown to be capable of differentiation and proliferation.

EXAMPLE 4

Osmotic Stress Enriches Stem Cell Numbers in Dental Follicle Cell Populations

A wide range of diseases and medical conditions can cause excessive loss of body fluid and lead to dehydration. Cell dehydration occurs when cells lose water by osmosis. Dehydration can result in tissue damage as well as cell death. Serving as a repair mechanism, stem cells should possess self protection from dehydration. To determine if stem cells survive better in dehydrating condition, a heterogeneous dental follicle cell population (DFSCs) collected and cultured in stem cell medium as described above was treated with a medium of different NaCl osmolality ranging from 404 to 925 mmol/kg. The results indicated that all cells died in medium of osmolality greater than 642 mmol/kg. (Data not shown) A small portion of cells survived in medium of osmolality from about 619 to about 623 mmol/kg, and these surviving cells showed a greater level of osteogenesis than the control DFCs when placed into osteogenesis induction medium for one week. (Data not shown) In addition, cells surviving from high osmolality medium were smaller in their average size. These results indicate that the high osmolality (osmotic stress) enriched the number of stem cells in the remaining population.

EXAMPLE 5

Hypoxia Enriches Stem Cell Numbers in Dental Follicle Cell Populations

To test the effects of hypoxia (low oxygen conditions) on the dental follicle cell population, DFSCs obtained as described above were seeded in t-25 flasks and cultured in hypoxia chambers containing 1% or 5% $O_2$ for 1 or 2 weeks. The cells cultured at the normal atmospheric condition (about 21% $O_2$) served as the control. Cell growth was monitored with an alamar blue assay as above. After the designated time of incubation, the surviving cells were subjected to differentiation (osteogenesis and adipogenesis) and gene expression studies. The results indicated that DFSCs showed a higher proliferation rate when cultured in 5% oxygen ($O_2$) as compared to being cultured in normal atmospheric conditions (approximately 21% $O_2$). In contrast, normal dental follicle cells (non-stem cells) show a similar growth rate in either hypoxia or normal conditions. Moreover, an increase in stem cell characteristics was seen in the dental follicle stem cells grown in 5% $O_2$. Specifically, dental follicle stem cells grown in 5% $O_2$ exhibited a higher capability of differentiation (e.g., possessing greater adipogenesis potential) than the cells grown in normal atmospheric conditions (controls). Alkaline phosphatase (ALP) staining indicated that the dental follicle stem cells subjected to hypoxic treatment (5% $O_2$) increased in number, as seen by an increase in the number of ALP-stained cells in comparison to the controls (21% $O_2$). (Data not shown) Moreover, there was an increase in the amount of ALP-staining of the hypoxia-treated cells, as compared to the controls. (Data not shown) Increased expression of surface ALP is a marker often used to identify stem cells. Normal dental follicle cells show no or very weak ALP staining. Thus growing the DFSCs at 5% $O_2$ resulted in an increase in the number of stem cells in the population.

EXAMPLE 6

An ALDH Substrate Enriches Stem Cell Numbers in Dental Follicle Cell Populations We also tested an ALDH substrate, 4-hydroperoxycyclophosphamide (4-HC), for elimination of non-stem cells in culture. DFSCs were cultured as described above and then treated with 4-HC at the concentrations of 5, 10, 15, 20 and 25 µM in α-MEM medium containing 20% FBS for 48 hours at 37° C. The majority of the cells were killed at a 4-HC concentration greater than 15 µM. The surviving cells then were collected and subjected to cell proliferation, differentiation, and gene expression assays as described above for evaluation of stem cell properties. Putative stem cells surviving from a 4-HC treatment expressed a high level of multiple stem cell markers, including Abcb1, Prom1, Notch 1, and CD34, as determined by RT-PCR and western blotting. On the average, about a 2 to 4-fold increase in expression of these markers was detected in the 4-HC surviving cells as compared to the original population. (Data not shown) In addition, 4-HC treatment did not adversely affect the proliferation of the cells. In fact, flow cytometry analysis indicated that the putative stem cells surviving from the 4-HC treatment have a higher proliferation rate than the original cell population not subjected to 4-HC treatment. When the same 4-HC treatment protocol was applied to the dental follicle cells (DFCs; non-stem cells), none of them survived.

REFERENCES CITED

Bianco P and Robey PG (2000). Marrow stromal stem cells. *J Clin Invest*, 105: 663-1668.

Bosshardt D D, Schroeder H E (1996). Cementogenesis reviewed: a comparison between human premolars and rodent molars. *Anat Rec* 245:267-292.

Braut A, Kollar E J, Mina M. (2003) Analysis of the odontogenic and osteogenic potentials of dental pulp in vivo using a Coll1-2.3-GFP transgene. *Int J Dev Biol*. 47: 281-292.

Cahill D R, Marks S C Jr (1980). Tooth eruption: evidence for the central role of the dental follicle. *J Oral Pathol* 9:189-200.

Cai J, Cheng A, Luo Y, Lu C, Mattson M P, Rao M S, Furukawa K (2004). Membrane properties of rat embryonic multipotent neural stem cells. *J Neurochem;* 88:212-226.

Caplan A I (1991) Mesenchymal stem cells. *J Orthop Res*. 9:641-650. 1991

Corti S, Locatelli F, Papadimitriou D, Donadoni C, Salani S, Del Bo R, Strazzer S, Bresolin N, Comi G P (2006) Identification of a primitive brain-derived neural stem cell population based on aldehyde dehydrogenase activity. *Stem Cells,* 24:975-85.

Diekwisch T G H (2001). The developmental biology of cementum. *Int J Dev Biol* 45:695-706.

Doyle L A, Ross D D (2003). Multidrug resistance mediated by the breast cancer resistance protein BCRP (ABCG2). *Oncogene,* 22:7340-7358.

Duailibi M T, Duailibi S E, Young C S, Bartlett J D, Vacanti J P, Yelick P C (2004). Bioengineered teeth from cultured rat tooth bud cells. *J Dent Res*. 83:523-528. 2004

Fischler M P, Reinhart W H (1997). Fever: friend or enemy? *Schweiz Med Wochenschr;* 127:864-870.

Gangopadhyay N N, Shen H, Landreneau R, Luketich J D, Schuchert M (2004). Isolation and tracking of a rare lymphoid progenitor cell which facilitates bone marrow transplantation in mice. *J Immunol Methods.;* 292:73-81.

Goodell M A, Brose K, Paradis G, Conner A S, Mulligan R C (1996). Isolation and functional properties of murine hematopoietic stem cells that are replicating in vivo. *J Exp Med.;* 183:1797-806.

Goodell M A, Rosenzweig M, Kim H, Marks D F, DeMaria M, Paradis G, Grupp S A, Sieff C A, Mulligan R C, Johnson R P (1997). Dye efflux studies suggest that hematopoietic stem cells expressing low or undetectable levels of CD34 antigen exist in multiple species. *Nat. Med*. 3, 1337-1345.

Goodwin H S, Bicknese A R, Chien S N, Bogucki B D, Quinn C O, Wall D A (2001). Multilineage differentiation activity by cells isolated from umbilical cord blood: expression of bone, fat, and neural markers. *Biol Blood Marrow Transplant*. 7:581-588.

Gronthos S, Mankani M, Brahim J, Robey P G, Shi S (2000). Postnatal human dental pulp stem cells (DPSCs) in vitro and in vivo. *Proc Natl Acad Sci USA.;* 97:13625-13630.

Gronthos S, Brahim J, Li W, Fisher L W, Cheman N, Boyde A, DenBesten P, Robey P G, Shi S (2002). Stem cell properties of human dental pulp stem cells. *J Dent Res*. 81:531-535.

Gregory C A, Gunn W G, Peister A, Prockop D J (2004). An Alizarin red-based assay of mineralization by adherent cells in culture: comparison with cetylpyridinium chloride extraction. *Anal Biochem*. 329:77-84.

Gussoni E, Soneoka Y, Strickland C D, Buzney E A, Khan M K, Flint A F, Kunkel L M, Mulligan R C (1999) Dystrophin expression in the mdx mouse restored by stem cell *Nature (London)* 401: 390-394.

Handa K, Saito M, Yamauchi M, Kiyono T, Sato S, Teranaka T et al. (2002). Cementum matrix formation in vivo by cultured dental follicle cells. *Bone* 31:606-611.

Harris M (1967). Growth inhibition in mammalian cells exposed to thermal stress. *Experientia*. 15; 23(7):563-564.

Hess D A, Wirthlin L, Craft T P, Herrbrich P E, Hohm S A, Lahey R, Eades W C, Creer M H, Nolta J A (2005). Selection based on CD133 and high aldehyde dehydrogenase activity isolates long-term reconstituting human hematopoietic stem cells. *Blood*. 107:2162-2169.

Hosaka S, Nakatsura T, Tsukamoto H, Hatayama T, Baba H, Nishimura Y (2006). Synthetic small interfering RNA targeting heat shock protein 105 induces apoptosis of various cancer cells both in vitro and in vivo. *Cancer Sci*. 97:623-632.

Hulspas R, Quesenberry P J (2000). Characterization of neurosphere cell phenotypes by flow cytometry. *Cytometry* 40: 245-250.

Hung S C, Chen N J, Hsieh S L, Li H, Ma H L, Lo W H (2002). Isolation and characterization of size-sieved stem cells from human bone marrow. *Stem Cells*. 20:249-58.

Iohara K, Zheng L, Ito M, Tomokiyo A, Matsushita K, Nakashima M (2006). Side population cells isolated from porcine dental pulp tissue with self-renewal and multipotency for dentinogenesis, chondrogenesis, adipogenesis, and neurogenesis. *Stem Cells*. 24: 2493-2503. 2006

Jackson K A, Mi T, Goodell M A (1999). Hematopoietic potential of stem cells isolated from murine skeletal muscle. *Proc. Natl. Acad. Sci. USA*. 96:14482-14486.

Jo Y Y, Lee H J, Kook S Y, Choung H W, Park J Y, Chung J H, Choung Y H, Kim E S, Yang H C, Choung P H (2007). Isolation and characterization of postnatal stem cells from human dental tissues. *Tissue Eng*. 13:767-773.

Kastan M B, Schlaffer E, Russo J E, Colvin O M, Civin C I, Hilton J (1990). Direct demonstration of elevated aldehyde dehydrogenase in human hematopoietic progenitor cells. *Blood* 75:1947-1950.

Krishnamurthy P, Ross D D, Nakanishi T, Bailey-Dell K, Zhou S, Mercer K E, Sarkadi B, Sorrentino B P, Schuetz J D (2004). The stem cell marker Bcrp/ABCG2 enhances hypoxic cell survival through interactions with heme. *J Biol. Chem.* 279:24218-24225.

Kuznetsov S A, Friedenstein A J, Robey P G (1997). Factors required for bone marrow stromal fibroblast colony formation in vitro. *Br J Haematol.* 97:561-570.

Leemhuis T, Yoder M C, Grigsby S, Aguero B, Eder P, Srour E F (1996). Isolation of primitive human bone marrow hematopoietic progenitor cells using Hoechst 33342 and Rhodamine 123. *Exp. Hematol.* 24:1215-1224.

Lennon D P, Edmison J M, Caplan A I (2001). Cultivation of rat marrow-derived mesenchymal stem cells in reduced oxygen tension: effects on in vitro and in vivo osteochondrogenesis. *J Cell Physiol.* 187:345-355.

Leong T W, Chew F T, Hutmacher D W (2004). Isolating bone marrow stem cells using sieve technology. Stem Cells. 22:1123-1125.

Li G C, Li L, Liu R Y, Rehman M, Lee W M (1992). Heat shock protein hsp70 protects cells from thermal stress even after deletion of its ATP-binding domain. *Proc Natl Acad Sci USA.* 89:2036-2040.

Lin K K, Goodell M A (2006). Purification of hematopoietic stem cells using the side population. *Methods Enzymol.* 420:255-264.

Lioznov M V, Freiberger P, Kroger N, Zander A R, Fehse B (2005). Aldehyde dehydrogenase activity as a marker for the quality of hematopoietic stem cell transplants. *Bone Marrow Transplant.* 35:909-914.

Liu D, Wise G E (2007). A DNA microarray analysis of chemokine and receptor genes in the rat dental follicle—Role of secreted frizzled-related protein-1 in osteoclastogenesis. *Bone.* 41: 266-272.

Liu H, Gronthos S, Shi S (2006). Dental pulp stem cells. *Methods Enzymol.* 419:99-113.

Liu J Q, Zhang W F, Jin J, Qian W B (2006). Inhibition effect of topotecan on human myelodysplastic syndrome cells in vitro and in vivo. *Zhejiang Da Xue Xue Bao Yi Xue Ban.* 35:127-131.

Luan X, Ito Y, Dangaria S, Diekwisch T G H (2006). Dental follicle progenitor cell heterogeneity in the developing mouse periodontium. *Stem Cells Dev* 15:595-608.

Marks S C Jr, Cahill D R (1984). Experimental study in the dog of the non-active role of the tooth in the eruptive process. *Arch Oral Biol* 29:311-322.

Mina M, Braut A (2004). New insight into progenitor/stem cells in dental pulp using Colla1-GFP transgenes. *Cells Tissues Organs.;* 176:120-133.

Miura M, Gronthos S, Zhao M, Lu B, Fisher L W, Robey P G, Shi S (2004). SHED: stem cells from human exfoliated deciduous teeth. *Proc Natl Acad Sci USA.* 100: 5807-5812.

Morsczeck C, Gotz W, Schierholz J, Zeilhofer F, Kuhn U, Mohl C, Sippel C, Hoffmann K H (2005). Isolation of precursor cells (PCs) from human dental follicle of wisdom teeth. *Matrix Biol.* 24:155-165.

Neuhaus O, Wiendl H, Kieseier B C, Archelos J J, Hemmer B, Stuve O, Hartung H P (2005). Multiple sclerosis: Mitoxantrone promotes differential effects on immunocompetent cells in vitro. *J Neuroimmunol.* 168:128-137.

Ohtani T, Nakamura T, Toda K, Furukawa F (2006). Cyclophosphamide enhances TNF-alpha-induced apoptotic cell death in murine vascular endothelial cell. *FEBS Lett.* 580: 1597-1600.

Orlic D, Fischer R, Nishikawa S, Nienhuis A W, Bodine D M (1993). Purification and characterization of heterogeneous pluripotent hematopoietic stem cell populations expressing high levels of c-kit receptor. *Blood.* 82:762-770.

Owen M, Friedenstein A J (1988). Stromal stem cells: marrow-derived osteogenic precursors. *Ciba Found Symp.* 136:42-60.

Parmar K, Sauk-Schubert C, Burdick D, Handley M, Mauch P (2003). Sca+CD34-murine side population cells are highly enriched for primitive stem cells. *Exp Hematol.* 31:244-250.

Pittenger M F, Mackay A M, Beck S C, Jaiswal R K, Douglas R, Mosca J D, Moorman M A, Simonetti D W, Craig S, Marshak D R (1999). Multilineage potential of adult human mesenchymal stem cells. *Science.* 284:143-147.

Raff M (2003). Adult stem cell plasticity: Fact or Artifact? *Annu Rev Cell Dev Biol.* 19:1-22.

Reali C, Scintu F, Pillai R, Cabras S, Argiolu F, Ristaldi M S, Sanna M A, Badiali M, Sogos V (2006). Differentiation of human adult C D34+ stem cells into cells with a neural phenotype: role of astrocytes. *Exp Neurol.* 197:399-406.

Redvers R P, Li A, Kaur P (2006). Side population in adult murine epidermis exhibits phenotypic and functional characteristics of keratinocyte stem cells. *Proc Natl Acad Sci USA.* 103:13168-13173.

Reya T, Morrison S J, Clarke M F, Weissman I L (2001). Stem cells, cancer, and cancer stem cells. *Nature.* 414:105-111.

Ross D D, Yang W, Abruzzo L V, Dalton W S, Schneider E, Lage H, Dietel M, Greenberger L, Cole S P, Doyle L A (1999). Atypical multidrug resistance: breast cancer resistance protein messenger RNA expression in mitoxantrone-selected cell lines. *J Natl Cancer Inst.* 91:429-433.

Russo J E, Hilton J, and Colvin O M (1989). The role of aldehyde dehydrogenase isozymes in cellular resistance to the alkylating agent cyclophosphamide. *Prog Clin Biol Res.* 290:65-79.

Saito M, Handa K, Kiyono T, Hattori S, Yokoi T, Tsubakimoto T et al. (2005). Immortalization of cementoblast progenitor cells with Bmi-1 and TERT. *J Bone Miner Res* 20:50-57.

Schaffner A (2006). Fever—useful or noxious symptom that should be treated? *Ther Umsch.* 63:185-18.

Seo B M, Miura M, Gronthos S, Bartold P M, Batouli S, Brahim J, Young M, Robey P G, Wang C Y, Shi S (2004). Investigation of multipotent postnatal stem cells from human periodontal ligament. *Lancet.* 364:149-155.

Seo B M, Sonoyama W, Coppe C, Miura M, Miura Y, Yamaza T, Lee J, and Shi S (2008). SHED repair critical-size calvarial defects in immunocompromised mice. *Oral Diseases.* 14(5):428-434.

Shi S, Bartold P M, Miura M, Seo B M, Robey P G (2005), Gronthos S. The efficacy of mesenchymal stem cells to regenerate and repair dental structures. *Orthod Craniofac Res.* 8:191-199.

Soszynski D (2003). The pathogenesis and the adaptive value of fever. *Postepy Hig Med. Dosw.* 57: 531-554.

Storms R W, Trujillo A P, Springer J B, Shah L, Colvin O M, Ludeman S M, Smith C (1999). Isolation of primitive human hematopoietic progenitors on the basis of aldehyde dehydrogenase activity. *Proc Natl Acad Sci USA.* 96:9118-9123.

Turner J G, Gump J L, Zhang C, Cook J M, Marchion D, Hazlehurst L, Munster P, Schell M J, Dalton W S, Sullivan D M (2006). ABCG2 expression, function, and promoter methylation in human multiple myeloma. *Blood.* 108: 3881-3889.

Uchida N, Fujisaki T, Eaves A C, Eaves C J (2001). Transplantable hematopoietic stem cells in human fetal liver have a CD34(+) side population (S P)phenotype. *J Clin Invest.* 108:1071-1077.

Vacanti M P, Roy A, Cortiella J, Bonassar L, Vacanti C A (2001). Identification and initial characterization of spore-like cells in adult mammals. *J Cell Biochem.* 80:455-460.

Wise G E, Frazier-Bowers S, D'Souza R N (2002). Cellular, molecular, and genetic determinants of tooth eruption. *Crit. Rev Oral Biol Med.* 13:323-334.

Wise G E, King G J (2008). Mechanisms of tooth eruption and orthodontic tooth movement. *J Dent Res;* 87:414-434.

Wise G E, Lin F, Fan W (1992) Culture and characterization of dental follicle cells from rat molars. *Cell Tissue Res.* 267: 483-492.

Wise G E, Yao S (2006). Regional differences of expression of bone morphogenetic protein-2 and RANKL in the rat dental follicle. *Eur J Oral Sci* 114:512-516.

Wise G E, Yao S, Odgren P R, Pan F (2005). CSF-1 regulation of osteoclastogenesis for tooth eruption. *J Dent Res* 84:837-841.

Wolf N S, Kone A, Priestley G V, Bartelmez S H (1993). In vivo and in vitro characterization of long-term repopulating primitive hematopoietic cells isolated by sequential Hoechst 33342-rhodamine 123 F AC S selection. *Exp. Hematol.* 21: 614-622.

Yao S, Liu D, Pan F, Wise G E (2006). Effect of vascular endothelial growth factor on RANK gene expression in osteoclast precursors and on osteoclastogenesis. *Arch Oral Biol.* 51:596-602.

Young H E, Duplaa C, Yost M J, Henson N L, Floyd J A (2004). Clonogenic analysis reveals reserve stem cells in postnatal mammals. II. Pluripotent epiblastic-like stem cells. *Anat Rec A Discov Mol Cell Evol Biol.* 277:178-203.

Yu J, Wang Y, Deng Z, Tang L, Li Y, Shi J, Jin Y (2007). Odontogenic capability: bone marrow stromal stem cells versus dental pulp stem cells. *Biol Cell.* 99: 465-474.

Zeichner-David M, Oishi K, Su Z, Zakartchenko V, Chen L-S, Arzate H, Bringas P Jr (2003). Role of Hertwig's epithelial root sheath cells in tooth root development. *Dev Dyn* 228: 651-663.

Zhou S, Schuetz J D, Bunting K D, Colapietro A M, Sampath J, Morris J J, Lagutina I, Grosveld G C, Osawa M, Nakauchi H, Sorrentino B P (2001). The ABC transporter Bcrp1/ABCG2 is expressed in a wide variety of stem cells and is a molecular determinant of the side-population phenotype. *Nat. Med.* 7:1028-1034.

The complete disclosures of all references cited in this specification are hereby incorporated by reference. Also incorporated by reference is the complete disclosure of the following: S. Yao et al., "Differentiation of Stem Cells in the Dental Follicle," Journal of Dental Research, vol. 87 (8), pp. 767-771 (2008). In the event of an otherwise irreconcilable conflict, however, the present specification shall control.

We claim:

1. A method to obtain a multipotent stem cell population that proliferates and differentiates into at least two cell types by increasing the percentage of stem cells in an adult mammalian heterogeneous cell population, said method comprising the following:
   A) isolating an adult heterogeneous cell population from a mammal, wherein said heterogeneous cell population consists of both multipotent stem cells and non-stem cells,
   B) exposing the isolated heterogeneous cell population to a stress of an osmolality between 619 and 623 mmol/kg sodium chloride, wherein such exposure occurs for duration of time such that the non-stem cells are selectively killed and the surviving cell population has a higher percentage of stem cells;
   C) culturing the surviving cell population to increase the number of multipotent stem cells; and
   D) verifying that the cultured multipotent stem population differentiates into two or more cell types selected from the group consisting of osteoblasts, adipocytes, neurons, and odontoblasts.

2. The method of claim 1, additionally comprising isolating the stem cells from the cultured surviving cell population with the higher percentage of stem cells.

3. The method of claim 1, wherein the heterogeneous population of cells is isolated from the group consisting of adult dental follicles, adult dental pulp, blood, skin, gut, testis, and other adult organs.

4. The method of claim 1, wherein the verification step (D) comprises further culturing the proliferated stem cell population from step (C) in a medium that induces cellular differentiation selected from group consisting of an adipogenic medium, an osteogenic medium, a neurogenic medium, and an odontogenic medium.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Primer for breast cancer resistance protein

<400> SEQUENCE: 1
agtccggaaa acagctgaga                                              20

<210> SEQ ID NO 2
<211> LENGTH: 20
<212> TYPE: DNA
<213> ORGANISM: Artificial sequence
<220> FEATURE:
<223> OTHER INFORMATION: Primer for breast cancer resistance protein

<400> SEQUENCE: 2
cccatcacaa cgtcatcttg                                              20

<210> SEQ ID NO 3
<211> LENGTH: 29
<212> TYPE: DNA
<213> ORGANISM: Artificial sequence
<220> FEATURE:
<223> OTHER INFORMATION: Primer for MDR1

<400> SEQUENCE: 3
ggaactctcg ctgctatcat ccacggaac                                    29

<210> SEQ ID NO 4
<211> LENGTH: 29

```
<212> TYPE: DNA
<213> ORGANISM: Artificial sequence
<220> FEATURE:
<223> OTHER INFORMATION: Primer for MDR1

<400> SEQUENCE: 4
acctggatgt aggcaacgat gagcacacc                                    29
```